United States Patent
Nawrocki et al.

(10) Patent No.: US 8,431,734 B2
(45) Date of Patent: Apr. 30, 2013

(54) PROCESS FOR THE PREPARATION OF N,N'-BIS(2-HYDROXYBENZYL)-ETHYLENEDIAMINE-N,N'-DIACETIC ACID AND ITS DERIVATIVES

(75) Inventors: Adam Nawrocki, Poznan (PL); Filip Stefaniak, Ostrzeszow (PL); Anika Mrozek-Niecko, Sierakow (PL); Radoslaw Olszewski, Sompolno (PL)

(73) Assignee: Przedsiebiorstwo Produkeyjno-Consultingowe Adob SP. Z O.O. SP. K., Poznan (PL)

( * ) Notice: Subject to any disclaimer, the term of this patent is extended or adjusted under 35 U.S.C. 154(b) by 350 days.

(21) Appl. No.: 12/671,316

(22) PCT Filed: Sep. 15, 2008

(86) PCT No.: PCT/EP2008/062269
§ 371 (c)(1),
(2), (4) Date: Feb. 12, 2010

(87) PCT Pub. No.: WO2009/037235
PCT Pub. Date: Mar. 26, 2009

(65) Prior Publication Data
US 2010/0168469 A1    Jul. 1, 2010

(30) Foreign Application Priority Data
Sep. 20, 2007 (EP) .................. 07465006

(51) Int. Cl.
*C07C 229/00* (2006.01)

(52) U.S. Cl.
USPC ...................................... 562/448

(58) Field of Classification Search .......... None
See application file for complete search history.

(56) References Cited

U.S. PATENT DOCUMENTS

| | | | |
|---|---|---|---|
| 2,967,196 A | 1/1961 | Kroll et al. | |
| 3,038,793 A | 6/1962 | Kroll et al. | |
| 3,632,637 A | 1/1972 | Martell | |
| 4,073,804 A * | 2/1978 | Hearon et al. | 562/575 |
| 4,129,556 A | 12/1978 | Zondler et al. | |
| 4,130,582 A | 12/1978 | Petree et al. | |
| 2001/0047108 A1 * | 11/2001 | McKearin | 562/443 |
| 2004/0259859 A1 * | 12/2004 | Coe et al. | 514/217.08 |

FOREIGN PATENT DOCUMENTS

| | | |
|---|---|---|
| EP | 0331556 A2 | 9/1989 |
| WO | 0146114 A1 | 6/2001 |

OTHER PUBLICATIONS

A.F. Abdel-Magid et al., "Reductive Amination of aldehydes and Ketones with Sodium Triacetoxyborohydride. Studies on Direct and Indirect Reductive Amination Procedures", J. Org. Chem., 61, 3849-3862 (1996).

J March et al., "Addition to Carbon-Hetero Multiple Bonds", Advanced Organic Chemistry, 3rd Ed., pp. 798-801 (1985).

F. Yunta et al., "Chelating Agents Related to Ethylenediamine Bis(2-hydroxyphenyl)acetic Acid (EDDHA): Synthesis, Characterization, and Equilibrium Studies of the Free Ligands and Their Mg2+, Ca2+, Cu2+, and Fe3+ Chelates", Inorganic Chem., vol. 42, No. 17, pp. 5412-5421 (2003).

Martel et al., "Synthesis of N,N1-di(2-hydroxybenzyl)ethylenediamine-N,N1-diacetic acid (HBED) and derivatives", Can. J. Chem., 64(3), pp. 449-456 (1986).

* cited by examiner

*Primary Examiner* — Susanna Moore
*Assistant Examiner* — Jennifer C Sawyer
(74) *Attorney, Agent, or Firm* — Fish & Richardson P.C.

(57) ABSTRACT

The invention relates to a process for the preparation of N,N'-bis(2-hydroxybenzyl)-ethylenediamine-N,N'-diacetic acid and its derivatives of general formula (I), wherein both R have the same meaning and are selected from H, $C_1$-$C_4$ alkyl, $CH_2OH$, $SO_3M$, and $COOM$; and all M have the same meaning and represent hydrogen atom, Na, K or $NH_4$; which comprises reductive amination of glyoxylic acid with a salan compound of general formula (II), in the presence of an amine proton acceptor. The compounds of formula (I) can be used as chelating agents for micronutrients in fertilizer preparations for plants.

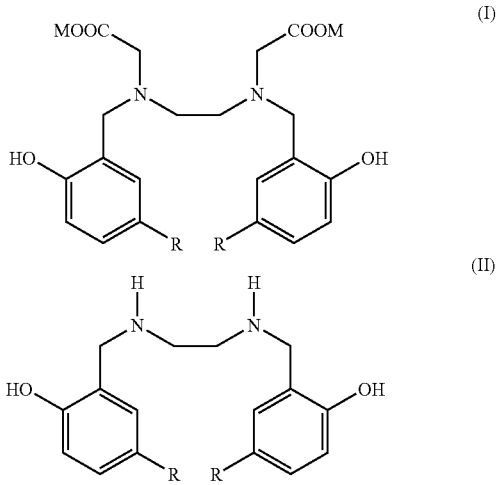

26 Claims, No Drawings

PROCESS FOR THE PREPARATION OF N,N'-BIS(2-HYDROXYBENZYL)-ETHYLENEDIAMINE-N,N'-DIACETIC ACID AND ITS DERIVATIVES

CROSS REFERENCE TO PRIOR APPLICATIONS

This is a U.S. National Phase application under 35 U.S.C. §371 of International Patent Application No. PCT/EP2008/062269, filed Sep. 15, 2008, and claims the priority of European Patent Application No. 07465006.0, filed Sep. 28, 2007 both of which are incorporated by reference herein. The International Application published in English on Mar. 26, 2009 as WO 2009/037235 under PCT Article 21(2).

The present invention relates to a process for the preparation of N,N'-bis(2-hydroxybenzyl)ethylenediamine-N,N'-diacetic acid and its derivatives substituted in phenyl ring, as well as their salts.

N,N'-Bis(2-hydroxybenzyl)ethylenediamine-N,N'-diacetic acid, also known under the name HBED, and its derivatives substituted in para position with respect to phenolic hydroxy group are well known for their ability to chelate III and IV groups of metal ions in aqueous solutions. They can be used as chelating agents for micronutrients in fertilizer preparations for plants, such as iron, zinc, copper or manganese micronutrients. Therefore a need exists of its industrial production in large scale.

One of known methods of the preparation of HBED is described in U.S. Pat. No. 3,632,637 and comprises reaction of disodium N,N'-ethylenediaminediacetate with o-acetoxybenzyl bromide or chloride and then alkaline hydrolysis to remove acetoxy protecting group. The preparation of o-acetoxybenzyl bromide is complex and requires two reaction steps: reaction of o-hydroxybenzyl alcohol with acetic anhydride to form o-acetoxybenzyl acetate and then bromination with HBr. Furthermore, as later reported by Martell et al in Can. J. Chem., vol. 63(3), 449-456, 1986, that procedure suffered from the formation of a resinous polymeric by-product, which seemed to be promoted by treatment with acid or base and sometimes formed spontaneously during recrystallization of the material. Another disadvantage of this method is that disodium N,N'-ethylenediamine-diacetate is not easy available and must be prepared in the reaction of carboxymethylation of ethylenediamine which involves the use of cyanides (NaCN) and $CH_2O$.

Martell et al in Can. J. Chem., vol. 63(3), 449-456, 1986 reports two approaches for the synthesis of HBED and derivatives. The first approach, which is suitable for synthesis of HBED, involves conversion of N,N'-bis(2-hydroxybenzyl)ethylenediamine to the amide via reaction with formaldehyde and HCN followed by hydrolysis. A disadvantage of this approach is the use of HCN and difficulty of hydrolyzing diamide, which requires the use of very pH sensitive metal catalysis. The second approach, which is suitable for synthesis of HBED derivatives substituted para to the phenolic hydroxy group, involves reaction of N,N'-ethylenediaminediacetic acid with para substituted phenols and formaldehyde and was found to be very sensitive to pH. Another disadvantage of this second approach is also the necessity of the synthesis of the starting N,N'-ethylenediaminediacetic acid.

Another synthetic approach for the preparation of HBED is described in WO01/46114 and comprises reaction of N,N'-bis(2-hydroxybenzyl)ethylenediamine with tert-butyl haloacetate and then hydrolysis of resulting N,N'-bis(2-hydroxybenzyl)ethylene-diamine-N,N'-diacetic acid di-tert-butyl ester with a weak acid, such as formic acid. The method was specifically designed to obtain neat HBED, which then could be easy converted into target mono-cationic salt while avoiding intermediate dihydrochloride formation and its neutralization into sodium chloride. However, the reaction of N,N'-bis(2-hydroxybenzyl)ethylenediamine acid with t-butyl bromoacetate is performed in DMSO solvent and takes a very long time. Hydrolysis with formic acid is also very time consuming and takes 5 days, the yield of hydrolysis being very low. Furthermore, t-butyl bromoacetate is expensive and not easy available on the industrial scale.

A synthetic approach for the preparation of HBED derivatives substituted in position para with respect to the phenolic OH group is known from U.S. Pat. No. 2,967,196 and U.S. Pat. No. 3,038,793 and comprises reacting formaldehyde with disodium N,N'-ethylene-diaminediacetate to form the dimethylol derivative which can condense in the position ortho to the phenolic OH group with para substituted phenols. A disadvantage of this method is that disodium N,N'-ethylenediaminediacetate must be prepared first in the reaction of carboxymethylation of ethylenediamine which involves the use of NaCN and $CH_2O$. This approach fails when applied to the preparation of HBED because of by-products formation due to the possibility of the reaction of methylolol group with phenol in positions both para and ortho to the phenolic OH group and formation of a complex mixture of compounds.

The object of the present invention is to provide a synthetic process, which applicable both for HBED itself and its derivatives substituted in para position with respect to phenolic OH group and which could be carried out in the same reaction system and under similar conditions both in the case of HBED and its derivatives.

It is also the object of the present invention to provide a synthetic process having small number of steps and employing reagents which are either easy available or easy to synthesize on a large scale, as well as standard and simple industrial operations and equipment. It is also the object of the invention to eliminate the need of using toxic cyanides.

In accordance with the invention there is provided a process for the preparation of N,N'-bis(2-hydroxybenzyl)ethylenediamine-N,N'-diacetic acid and its derivatives of general formula I:

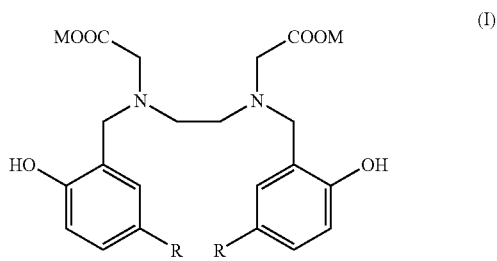

wherein:
both R have the same meaning and are selected from H, $C_1$-$C_4$alkyl, $CH_2OH$, $SO_3M$, and COOM; and
all M have the same meaning and represent hydrogen atom, Na, K or $NH_4$;
which comprises:
reductive amination of glyoxylic acid with a salan compound of formula (II)

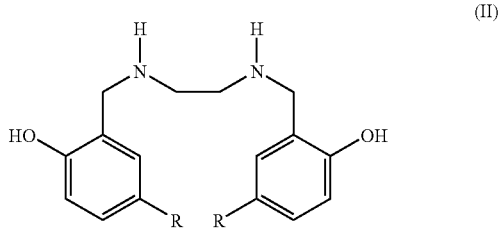

(II)

wherein R have the same meaning as defined above for formula (I), in the presence of an amine proton acceptor, to obtain the compound of formula (I), wherein M are hydrogen atoms, and if desired, converting it further into compound of formula (I) wherein M represent Na, K or $NH_4$ by the treatment with a corresponding base.

The term $C_1$-$C_4$alkyl group in the above formulas encompasses both straight (linear) or branched $C_1$-$C_4$alkyl group, such as methyl, ethyl, n-propyl, iso-propyl, n-butyl, sec-butyl, tert-butyl.

The most preferred compounds prepared by the process of the invention are compounds of formula (I) wherein R are hydrogen atoms or methyl groups.

The molar ratio salan compound:glyoxylic acid:amine is in the range from 1:2:2 to 1:4:5, preferably 1:3:3.5.

Any excess of reagents used in the reductive amination in the process of the invention can be easily recovered from the reaction medium after the reaction and used in a next batch of the reductive amination. The only inorganic by-product in the process is a salt, contrary to the processes known from the prior art.

Reductive amination can be preferably carried out by catalytic hydrogenation (reaction with hydrogen) in the presence of a hydrogenation catalyst.

For the catalytic hydrogenation the starting salan compound of formula (I)) can be dissolved in a polar solvent, preferably selected from $C_1$-$C_3$ alkanol or their mixtures or in a $C_1$-$C_3$ alkanol/water mixture containing 30 to 60% of the alkanol. Preferred solvent can be methanol, ethanol in a mixture with water and methanol, such as industrial methylated spirit. Then the solution of glyoxylic acid and amine in the same solvent is introduced to the solution of the salan compound. The molar ratio of glyoxylic acid to amine is about 1:1 or an excess of amine can be used.

Reductive amination can be also carried out in an aqueous-amine proton acceptor medium. In such a case the reaction is performed in a heterogeneous medium, where the mixture of glyoxylic acid and amine is dissolved in the aqueous phase and the salan compound and the catalyst remain undissolved.

The hydrogenation catalyst can be selected from conventional catalysts which include, without limitation, catalysts based on noble or transition metals such as palladium, platinum, rhodium, nickel, osmium and ruthenium. These catalysts can be used in a form bound to a support, carbon or charcoal being the supports most commonly used. The most preferred are Raney nickel (Ra—Ni) and palladium or platinum on a charcoal (Pd/C, Pt/C). Hydrogenation is carried out by mixing reagents in a solvent in the atmosphere of hydrogen gas. The choice of a solvent, temperature of the reaction and the hydrogen pressure depends on a specific catalyst employed. Hydrogenation can be carried out under low hydrogen pressure of about 1 to 4 atm and relatively low temperature (typically when noble metals catalysts, such as platinum, are used) or under low- or medium pressure such as 30 to 50 atm (when Ra—Ni or Rh/C are used). Preferred catalysts are Pd/C or Ra—Ni, preferably in the amount of 1 to 5% by weight with respect to the starting salan compound.

Hydrogenation can be carried out at 30 to 70° C., preferably at about 50° C., until the hydrogen absorption ceases. The time of the reaction is usually 4 to 48 hrs.

Glyoxylic acid can be used in any convenient and commercially available form, preferably as free acid or its hydrate, like monohydrate, or their mixtures. It can be also used as its salt, such as sodium salt hydrate, like monohydrate. Preferably, glyoxylic acid monohydrate is used when reductive amination is carried out in alcoholic medium. Aqueous 50% solution is used preferably when the reaction is carried out in water. When the reaction is carried out in an alcoholic solvent, glyoxylic acid can also be present at least in part in a form of its acetal or hemiacetal. The use of glyoxylic acid ester is also contemplated by the invention. By "glyoxylic acid" any form thereof as described above or their mixtures are understood in accordance with the invention.

The amine proton acceptor can be any amine compound capable of binding proton in a reaction media, most preferably simple tertiary amine such as triethylamine or tributylamine. Amine serves also as a blocking agent for carboxylic group in glyoxylic acid.

The compound of formula (I) wherein M are H is isolated in a form of a free acid or its monohydrochloride after separation of the hydrogenation catalyst by pressure filtration and subsequent evaporation of a solvent from the filtrate. The product in a monohydrochloride form can be crystallized from water after acidification to pH=1.5 to 2.5 with hydrochloric acid. Conversion of the compound of formula (I) wherein M are H into its salt, i.e. the compound of formula (I) wherein M represent Na, K or $NH_4$ is carried out by the treatment with a corresponding base to pH 10-12.5, preferably 11.5. Such corresponding bases are preferably sodium, potassium or ammonium hydroxides. After alkalization, 10 to 35% (by weight) aqueous solutions of the compound of formula (I) with M being Na, K or $NH_4$ are obtained, preferably 20% by weight.

The starting salan compounds of formula (II) can be prepared in two ways.

According to one approach, the starting salan compound of formula (II) can be prepared by condensation of ethylenediamine with 2 molar equivalents of salicylaldehyde or a corresponding salicylaldehyde derivative substituted with R substituent in position para with respect to hydroxy group and then reduction of thus obtained salen compound (Schiff's base). According to the second approach, the starting salan compound of formula (II) can be prepared by reaction of ethylenediamine, a formaldehyde source and phenol or phenol substituted with R substituent in para position (direct Mannich condensation). The second approach is applicable most preferably when R is $C_1$-$C_4$alkyl.

Therefore, in one variant of the invention, the process for the preparation of the compound of formula (I) wherein R are as described above comprises preparing salan compound of formula (II) by reaction of ethylenediamine with 2 molar equivalents of a compound of formula (IV)

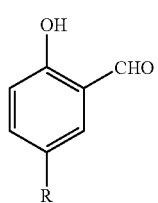

wherein R are as described for formula (I) above to obtain a corresponding compound of formula (V) wherein R are as described for formula (I)

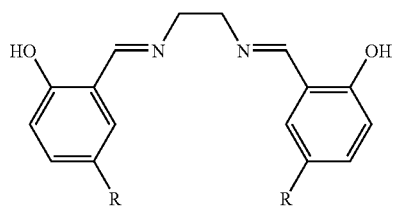

and then reduction of the compound of formula (V) to obtain the compound of formula (II).

Compounds of formula (IV), i.e. salicylaldehyde and its derivatives substituted with R substituent in position para with respect to hydroxy group, are well known and easy commercially available materials.

Reaction of ethylenediamine with the compound of formula (IV) can be carried out in a known manner in a suitable solvent, such as lower alcohols or their mixtures at an ambient temperature.

Reduction of the compound of formula (V) to obtain the compound of formula (II) can be generally carried out using any known reduction methods known in the art. One of such methods is the reduction with complex alkali metals hydrides, such as borohydrides, preferably sodium borohydride and lithium aluminium hydride. Preferred method of reduction is catalytic hydrogenation using the methods an catalysts as described above for the reaction of reductive amination of glyoxylic acid.

Most preferably, the reduction of the compound of formula (V) can be carried out by catalytic hydrogenation using hydrogen in the presence of a catalyst, such as palladium or nickel catalyst, like Pd/C or Ra—Ni. When the reduction is carried out by catalytic hydrogenation, intermediate compound of formula (II) without its isolation from the reaction medium can be directly reacted further with glyoxylic acid in the reductive amination in the same hydrogenation environment.

The yields of both the reaction of ethylenediamine with the compound of formula (IV) and the reduction of the intermediate compound of formula (V) are in principle quantitative. A further advantage is that reduction of the intermediate compound of formula (V) to form the compound of formula (II) and subsequent reductive amination of glyoxylic acid with the compound of formula (II) can be carried out under the same conditions and in the same equipment and using the same operations, which simplifies the whole process and lowers its costs.

An embodiment of the invention is therefore a process for the preparation of the compound of formula (I) wherein R are as described above, which comprises:

a) reaction of ethylenediamine with 2 molar equivalents of a compound of formula (IV)

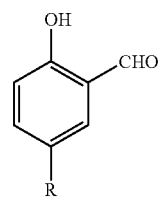

wherein R are as described for formula (I) above,
to obtain a corresponding compound of formula (V) wherein R are as described for formula (I)

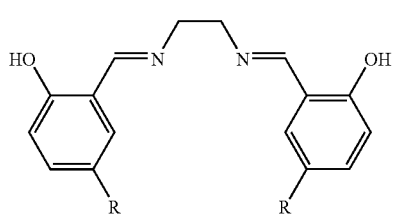

b) reduction of the compound of formula (V) to obtain the compound of formula (II) wherein R are as described above;

c) reductive amination of glyoxylic acid with a salan compound of general formula (II)

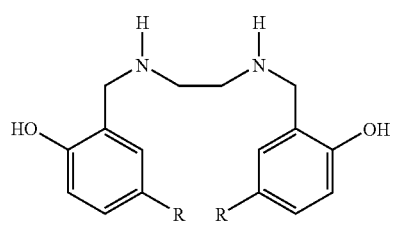

wherein R have the same meaning as defined above for formula (I), in the presence of an amine proton acceptor, to obtain the compound of formula (I), wherein M are hydrogen atoms, and d) if desired, further converting the compound of formula (I) wherein M are hydrogen atoms into compound of formula (I) wherein M represent Na, K or $NH_4$ by the treatment with a corresponding base.

Preferably, in the above embodiment the reduction in step b) and the reductive amination in step c) are carried out in the same reaction vessel, without isolation of the intermediate compound of the formula (II).

Also preferably, all steps a) to c) can be carried out in the same reaction vessel, without isolation of intermediate compounds of the formula (V) and (II).

Also preferably, both the reduction in step b) and the reductive amination in step c) are carried out by hydrogenation with hydrogen in the presence of a hydrogenation catalyst in a C₁-C₃ alkanol or their mixtures or in a C₁-C₃ alkanol/water mixture. Preferred hydrogenation catalysts are Ra—Ni and Pd/C.

In a second variant of the invention, a process for the preparation of a compound of formula (I) wherein R is C₁-C₄alkyl comprises preparing a starting salan compound of formula (II) wherein R is C₁-C₄alkyl by reaction of ethylenediamine, a formaldehyde source and a phenol compound of formula (III)

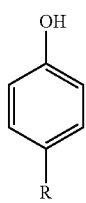

(III)

wherein R is C₁-C₄alkyl, at a molar ratio ethylenediamine: formaldehyde:phenol compound about 1:2:2.

An embodiment of the invention is therefore a process for the preparation of N,N'-bis(2-hydroxybenzyl)ethylenediamine-N,N'-diacetic acid and its derivatives of general formula I:

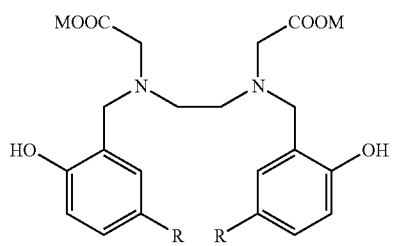

(I)

wherein:

both R have the same meaning and are selected from C₁-C₄alkyl; and all M have the same meaning and represent hydrogen atom, Na, K or NH₄; which comprises:

a) reaction of ethylenediamine, a formaldehyde source and the phenolic compound of formula (III)

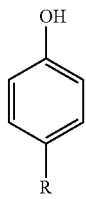

(III)

wherein R is C₁-C₄alkyl, in a molar ratio ethylenediamine: formaldehyde:phenol compound of formula (III) of about 1:2:2, to obtain the salan compound of general formula (II)

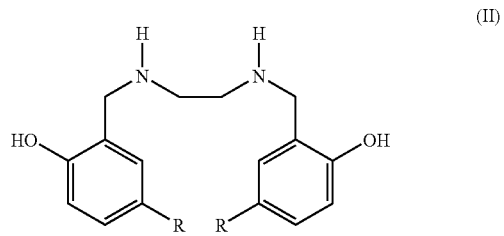

(II)

wherein R have the same meaning as defined for formula (I), and b) reductive amination of glyoxylic acid with the salan compound of the formula (II) in the presence of an amine proton acceptor, to obtain the compound of formula (I), wherein M are hydrogen atoms, and c) if desired, converting it further into compound of formula (I), wherein M represent Na, K or NH₄ by the treatment with a corresponding base.

Phenol compounds of formula (III) are known and commercially available.

The formaldehyde source can be any conventional and commercially available formaldehyde source such as an aqueous formaldehyde solution, paraformaldehyde, trioxane or hexamethylenetetraamine HMTP (urotropine). Preferred formaldehyde source is the aqueous 35-40% formaldehyde solution, usually sold as a saturated aqueous solution with formaldehyde concentration of about 37%, stabilized with 10-15% methanol (formalin or formol).

Most preferred formaldehyde sources are 37% aqueous formaldehyde solution and paraformaldehyde.

The reaction of ethylenediamine, the formaldehyde source and the phenol compound of formula (III) (direct Mannich condensation) can be carried out in a water-alcoholic mixture at reflux temperature, The product of formula (II) can be separated from the reaction mixture as its hydrochloride or by evaporation of a solvent. The yield of the Mannich condensation is 80 to 95%.

The Examples which follow illustrate the invention without any intention to limit its scope to the embodiments shown in these Examples.

EXAMPLE 1

General method of the preparation of compounds of formula (I) where R is C₁-C₄alkyl, using salan compounds prepared by direct Mannich condensation To a 250 ml flask equipped with a mechanical stirrer and reflux condenser 100 ml of a solvent and 0.1 mol of ethylenediamine are introduced to obtain a solution. To the solution 0.2 mol of paraformaldehyde/37% formaldehyde aqueous solution and 0.2 to 0.4 ml of 37% hydrochloric acid are added portionwise. The mixture obtained is heated for 0.5 h at 50-60° C. until complete homogeneity and then 50% solution of the phenol compound of formula (III) in the same solvent is added at the rate of 0.1 mol/h. The reaction mixture is heated at reflux for 4 to 30 h.

Salan compound of formula (II) thus obtained can be separated by crystallization:

in a form of a salan monohydrochloride after acidification of the reaction mixture to pH 0.5-2.0 with concentrated hydrochloric acid, or in a form of a salan after evaporation of the solvent and crystallization from ethyl ether at 5 to 10° C.

Reductive amination can be performed in a closed reaction medium, such as heated autoclave equipped with a mechanical stirrer. Salan compound and the mixture containing glyoxylic acid, an amine and a solvent are introduced to the autoclave. After completing the addition of the total amount of salan compound the reaction mixture contains reactants salan:glyoxylic acid:amine at the molar ratio in the range from 1:2:2 to 1:4:5. The total concentration of reactants in the reaction mixture is in the range 2 to 10% by weight.

Then to the reaction mixture a catalyst is added, which is preferably Ni-Raney or Pd/C in the amount of 1 to 5% by weight with respect to the salan compound.

The air is removed from the reaction system using the flow of an inert gas, preferably argon, and the autoclave is pressurized with hydrogen gas.

Reductive amination is carried out for 4 to 48 h at the hydrogen pressure of 2 to 50 atm.

The product is isolated by filtration of the catalyst, evaporation of the solvent and crystallization of the product from water after acidifying the to the pH 1.5 to 2.5.

The overall yield after crystallization is in the range from 30 to 85%, depending on the type of the phenol compound of formula (III) used in the reaction. Structures of the products are confirmed by means of $^1$H NMR analysis and their purities by means of HPLC and elemental analysis.

EXAMPLE 2

N,N'-Bis(2-hydroxy-5-methylbenzyl)ethylenediamine-N,N'-diacetic acid, monohydrochloride trihydrate

2.1. N,N'-bis(2-hydroxy-5-methylbenzyl)ethylenediamine (salan compound)

Following the general procedure described in Example 1 ethylenediamine (6.0 g, 0.1 mol), 37% formaldehyde aqueous solution (14.9 ml, 0.2 mol), p-cresol (21.6 g, 0.2 mol) and ethanol (150 ml) as a solvent were introduced to the reaction system to form a homogenous reaction mixture. The reaction mixture was heated at 60° C. for 12 h. The progress of the reaction was monitored by means of TLC analysis with ethanol:chloroform (9:2) developing system. When the completion of the reaction was confirmed, 9.2 ml (0.11 mol) of 37% hydrochloric acid was added dropwise to obtain pH=2.5. After 6 h of crystallization at ambient temperature white solid was obtained, which was filtered and washed three times with ethanol. The yield of the raw product so obtained was 24.6 g (82%). The raw product was then crystallized from the ethanol:water mixture, filtered and washed with ethanol (50 ml). The isolated product was dried in vacuum drier at 50° C. for 3 h. The yield of crystallization was 70%.

The structure of N,N'-bis(2-hydroxy-5-methylbenzyl)ethylenediamine so obtained was confirmed by means of $^1$H NMR. HPLC analysis shown the purity at the level of 96%.
$^1$H NMR (CDCl$_3$) δ: 7.26-6.72 (m, 8H, ArH), 3.95 (s, 4H, NCH$_2$CH$_2$), 2.82 (s, 4H, ArCH$_2$N), 2.24 (s, 6H, CH$_3$Ar)

2.2. N,N'-Bis(2-hydroxy-5-methylbenzyl)ethylenediamine-N,N'-diacetic acid, monohydrochloride trihydrate The salan compound obtained as described above in 2.1. (3 g, 0.01 mol) was qualitatively transferred to an autoclave containing methanol (100 ml), Pd/C (0.05 g) and the mixture of glyoxylic acid monohydrate (2.8 g, 0.03 mol) with triethylamine (4.0 g, 0.04 mol) in methanol (40 ml) was added to obtain a final molar ratio 1:3:4 (salan:glyoxylic acid:triethylamine). The air remaining over the reaction mixture was removed using the flow of argon stream.

The reaction system was heated to 50° C. and hydrogen was introduced at the pressure of 5 atm. The reaction of reductive amination was carried with stirring at 50° C. out for 20 h. When the reaction was completed, the catalyst was filtered under vacuum and the solvent evaporated by means of a rotary vacuum evaporator. The solid obtained was dissolved in water and acidified with 10% hydrochloric acid until pH=2.0. The crystallization was then carried out at 8° C. for 16 h.

3.8 g of the product was isolated (the yield 83%). The raw product was then crystallized at ambient temperature from the 85% ethanol. 2.8 g of the product was obtained after crystallization. The structure of the product N,N'bis(2-hydroxy-5-methylbenzyl)ethylenediamine-N,N'-diacetic acid.HCl.3H$_2$O was confirmed by means of $^1$H NMR and its purity by means of elemental analysis.
$^1$H NMR (DMSO) δ: 7.03-6.86 (m, 8H, ArH), 4.01 (s, 4H, HOOCCH$_2$N), 3.64 (s, 4H, ArCH$_2$N), 3.21 (s, 4H, NCH$_2$CH$_2$), 2.14 (s, 6H, CH$_3$Ar)
Elemental analysis: Calculated for C$_{22}$H$_{28}$N$_2$O$_6$.HCl.3H$_2$O:
C, 52.12; H, 6.96; N, 5.53. Found: C, 52.02; H, 7.01; N, 5.49.

EXAMPLE 3

N,N'-Bis(2-hydroxy-5-propylbenzyl)ethylenediamine-N,N'-diacetic acid, monohydrochloride trihydrate

3.1. N,N'-bis(2-hydroxy-5-propylbenzyl)ethylenediamine (salan compound)

Following the general procedure described in Example 1, in a reaction system equipped with a reflux condenser and Dean-Stark trap ethylenediamine (6.0 g, 0.1 mol), 37% formaldehyde aqueous solution (14.9 ml, 0.2 mol), 4-propylphenol (27.2 g, 0.2 mol), toluene (200 ml) as a solvent and 37% hydrochloric acid (0.3 ml) were introduced to form a homogenous reaction mixture. The reaction mixture was heated at 90-95° C. for 4 h. The progress of the consumption of the reactants was monitored by measuring the amount of water formed in the reaction and collected in a Dean-Stark trap. When the reaction stopped, the mixture was heated for additional 2 h at 110-112° C. Then the solvent was evaporated from the reaction mixture and a thick oil obtained was washed twice with hexane at reflux temperature. 26.4 g of the raw product in a form of the thick oil was obtained with the yield 74%. The raw product was then dissolved in 150 ml of ethanol and acidified with 9.2 ml (0.11 mol) of 37% hydrochloric acid to pH=2.0. The white solid which precipitated was filtered under vacuum and then crystallized from ethanol-water system and filtered and washed with 50 ml of ethanol. The product was dried in vacuum for 3 h at 50° C. The yield of crystallization was 63%.

The structure of N,N'-bis(2-hydroxy-5-propylbenzyl)ethylenediamine product so obtained was confirmed by means of $^1$H NMR. HPLC analysis shown the purity at the level of 97%.
$^1$H NMR (CDCl$_3$) δ: 7.26-6.72 (m, 8H, ArH), 3.95 (s, 4H, NCH$_2$CH$_2$), 2.82 (s, 4H, ArCH$_2$N), 2.45 (s, 6H, CH$_2$Ar), 1.61 (q, 4H, CH$_2$CH$_2$Ar), 0.92 (t, 6H, CH$_3$).

3.2. N,N'-Bis(2-hydroxy-5-propylbenzyl)ethylenediamine-N,N'-diacetic acid, hydrochloride trihydrate The salan compound obtained as described in 3.1. above (3 g, 0.01 mol) was qualitatively transferred to an autoclave containing methanol (100 ml), Pd/C (0.15 g) and the mixture of glyoxylic acid monohydrate (2.8 g, 0.03 mol) with triethylamine (4.0 g, 0.04 mol) in methanol (50 ml) was added. The air remained over the reaction mixture was removed using the argon flow.

The reaction system was heated to 50° C. and hydrogen gas was introduced at the pressure of 4 atm. The reaction of reductive amination was carried out at 50° C. for 20 h. When the reaction was completed, the catalyst was filtered under vacuum and the solvent evaporated by means of a rotary vacuum evaporator. The solid residue obtained was dissolved in water and acidified with 10% hydrochloric acid up to pH=2.0. The crystallization was then carried out at 8° C. for 16 h.

2.6 g of the product was isolated with the yield 45%. The raw solid product was then crystallized from the ethanol: water system. 1.8 g of the solid product was obtained. The identity of the product N,N'-bis(2-hydroxy-5-propylbenzyl)ethylenediamine-N,N'-diacetic.HCl.3H$_2$O acid was confirmed by means of $^1$H NMR and the purity by means of elemental analysis.

$^1$H NMR (DMSO) δ: 7.03-6.86 (m, 8H, ArH), 4.01 (s, 4H, HOOCCH$_2$N), 3.64 (s, 4H, ArCH$_2$N), 3.21 (s, 4H, NCH$_2$CH$_2$), 2.54 (t, 6H, CH$_2$Ar), 1.58 (q, 4H, CH$_2$CH$_2$Ar), 0.98 (t, 6H, CH$_3$)

Elemental analysis: Calculated for C$_{26}$H$_{36}$N$_2$O$_6$.HCl.3H$_2$O: C, 55.46; H, 7.70; N, 4.98,
Found: C, 55.42; H, 7.79; N, 4.99.

EXAMPLE 4

N,N'-Bis(2-hydroxy-5-methylbenzyl)ethylenediamine-N,N'-diacetic acid, monohydrochloride trihydrate Following the general procedure described in Example 1 ethylenediamine (0.1 mol) and 37% formaldehyde aqueous solution (0.2 mol) were added to the autoclave. The reaction mixture was heated at 80° C. until it became homogenous. Then p-cresol (0.2 mol) was added dropwise at 50° C. and the neat reaction mixture (with no solvent added) was heated at 90-95° C. for 16 h. The conversion of reactants was monitored by means of TLC analysis with ethanol:chloroform (9:2) developing system. When the completion of the reaction was confirmed, water was decanted from the reaction mixture and the oil thus obtained was washed twice with hexane and three times with water at reflux temperature. The remaining solvent was removed on the rotary evaporator. The raw product was obtained with the yield of 66% and then dissolved in ethyl ether and left for crystallization. White solid thus obtained was filtered under vacuum and washed with 60 ml of ethanol, then dried in vacuum dryer for 2 h at 40° C. Subsequently it was crystallized from ethyl ether with the yield 83%.

The structure of N,N'-bis(2-hydroxy-5-methylbenzyl)ethylenediamine product thus obtained was confirmed by means of $^1$H NMR. HPLC analysis shown the purity level of 98%.

Reductive amination carried out for 36 h following the procedure described above in Example 2.1. above gave the product with the isolated yield 90%. N,N'-bis(2-hydroxy-5-methylbenzyl)ethylenediamine-N,N'-diacetic acid monohydrochloride obtained after crystallization from ethanol:water system has the HPLC purity at the level of 96%.

EXAMPLE 5

General procedure for the preparation of compounds of formula (I) using salan compounds of formula (II) prepared by reduction of salen compounds of formula (V)

A. Preparation of a Salen Compound

To the round-bottomed 250 ml flask equipped with a mechanical stirrer and a reflux condenser 100 ml of a solvent and 0.1 mol of ethylenediamine is introduced to obtain a solution. To the solution 0.2 mol of salicylaldehyde or its derivative of the formula (IV) are added portionwise. The mixture obtained is heated for 1 h at 50-60° C. As the reaction progresses a salen compound produced precipitates in a form of a fine crystalline solid.

B. Reduction of a Salen Compound

When the reaction is completed, the mixture containing the salen compound is transferred to a heated autoclave with a mechanical stirrer and hydrogenation catalyst is added in the amount of 1 to 5% by weight with respect to the salen compound. The air is removed from the reaction system by passing inert gas flow (preferably argon), the autoclave is pressurized with hydrogen gas and the hydrogenation is then carried out at 40-60° C. at the hydrogen pressure 2 to 20 atm for 4 to 25 h until the absorption of hydrogen in the system ceases.

C. Reductive Amination with Glyoxylic Acid

The salan compound prepared as above and the mixture glyoxylic acid/amine are added to an autoclave in the amounts such as to obtain the final molar ratio salan:glyoxylic acid:amine in the range from 1:2:2 to 1:4:5. The total concentration of reactants in the reaction mixture is in the range 2 to 20% by weight.

Then to the reaction mixture a heterogeneous catalyst is added, preferably Ni-Raney or Pd/C in the amount of 1 to 5% by weight with respect to the salan compound.

The air is removed from the reaction system by venting and passing over inert gas flow (preferably argon). Reductive amination is carried out for 4 to 48 h at the hydrogen pressure of 2 to 50 atm.

The product is isolated by filtration of the catalyst, evaporation of the solvent and crystallization of the product from water after acidifying to the pH 1.5 to 2.5.

If both the preparation of salan compound and its reduction are carried out in water, the salan compound produced is separated directly from the reaction mixture by acidification with a mineral acid, preferably with hydrochloric acid.

Structures of the products are confirmed by means of $^1$H NMR analysis and their purities by means of HPLC and elemental analysis.

EXAMPLE 6

N,N'-bis(2-hydroxybenzyl)ethylenediamine-N,N'-diacetic acid monohydrochloride trihydrate Following the general procedure described above in Example 5, ethylenediamine (6.0 g, 0.1 mol), salicylaldehyde (24.4 g, 0.2 mol) and methanol (120 ml) were added to an autoclave. The reaction mixture was heated at 50° C. for 3 h. The reaction progress was monitored by means of TLC analysis with ethanol:chloroform (9:2) developing system. When the completion of the reaction was confirmed the sample of a salen compound was isolated to perform the $^1$H NMR analysis and confirm the structure of the product obtained.

¹H NMR (CDCl₃) δ: 13.2 (s, 2H, OH), 8.35 (s, 2H, ArCHN), 7.32-6.83 (m, 8H, ArH), 3.93 (s, 4H, NCH$_2$CH$_2$).

Then to the autoclave 0.2 g of the Pd/C was introduced, the air was removed and the reaction was carried out at 50° C. in the atmosphere of hydrogen gas under the pressure 5 atm for 3 h. When hydrogen absorption ceased the mixture of glyoxylic acid monohydrate (27.6 g, 0.3 mol) and triethylamine (40.4 g, 0.4 mol) in methanol (100 ml) was introduced to the salan compound.

The reaction system was heated to 50° C. and hydrogen was introduced under the pressure of 10 atm. The reductive amination was carried out for 15 h, then the catalyst was filtered and the solvent evaporated by means of a rotary vacuum evaporator. The solid (62 g) obtained was dissolved in water and acidified with 10% hydrochloric acid to pH=2.0. Crystallization was carried out for 12 h at 8° C.

37 g of the product N,N'-bis(2-hydroxybenzyl)ethylenediamine-N,N'-diacetic acid monohydrochloride trihydrate was separated with the overall yield 78% with respect to the starting ethylenediamine. The raw product was recrystallized form 85% ethanol. The structure of the product was confirmed by means of ¹H NMR and the purity thereof by means of elemental analysis.

¹H NMR (DMSO) δ: 7.23-6.78 (m, 8H, ArH), 4.06 (s, 4H, HOOCCH$_2$N), 3.65 (s, 4H, ArCH$_2$N), 3.22 (s, 4H, NCH$_2$CH$_2$)

Elemental analysis: Calculated for C$_{20}$H$_{24}$N$_2$O$_6$.HCl.3H$_2$O: C, 50.16; H, 6.52; N, 5.85,
Found: C, 50.15; H, 6.58; N, 5.81.

EXAMPLE 7

N,N'-bis(2-hydroxybenzyl)ethylenediamine-N,N'-diacetic acid monohydrochloride trihydrate Following the general procedure described in Example 5 ethylenediamine (6 g, 0.1 mol), salicylaldehyde (24.4 g, 0.2 mol) and water (100 ml) were added to the autoclave. The reaction mixture was heated at 45° C. for 5 h. The reaction progress was monitored by means of TLC analysis with ethanol:chloroform (9:2) developing system. When the completion of the reaction was confirmed the sample of a product was isolated to perform the ¹H NMR analysis and confirm the structure of the obtained salen product (analysis consistent with the data presented in Example 6).

Then to the autoclave 0.1 g of the Pd/C was introduced, the air was removed, the autoclave was pressurized with hydrogen and the reaction was carried out at 45-50° C. under the hydrogen pressure of 6 atm for 14 h. When the absorption of hydrogen ceased, methanol (180 ml) and the mixture of glyoxylic acid monohydrate (27.8 g, 0.3 mol) and triethylamine (40.5 g, 0.4 mol) were introduced to the system.

The reaction system was heated to 50° C. and hydrogen was introduced under the pressure of 10 atm. The reductive amination was carried out for 15 h, then the catalyst was filtered and the solvent evaporated by means of a rotary vacuum evaporator. The solid obtained was dissolved in water and acidified with 10% hydrochloric acid to pH=2.0. Crystallization was carried out for 10 h at 8° C.

35.5 g of the product N,N'-bis(2-hydroxybenzyl)ethylenediamine-N,N'-diacetic acid hydrochloride trihydrate was separated with the overall yield 84% with respect to the starting ethylenediamine. The raw product was recrystallized form the 85% ethanol. The structure of the product was confirmed by means of ¹H NMR and the purity thereof by means of elemental microanalysis.

EXAMPLE 8

N,N'-bis(5-carboxy-2-hydroxybenzyl)ethylenediamine-N,N'-diacetic acid monohydrochloride trihydrate The above product was prepared following the general procedure described in Example 5 and using 3-formyl-4-hydroxybenzoic acid as a starting material for the preparation of salen compound. Condensation of 3-formyl-4-hydroxybenzoic acid with ethylenediamine and reduction of resulting salen compound to the salan compound were carried out in iso-propanol with the total yield 62%.

The salan product was isolated from the reaction mixture and reductive amination was carried out in water using 50% aqueous solution of glyoxylic acid and tributylamine at the molar ratio salan compound:glyoxylic acid:tributylamine equal to 1:2.5:3. The reductive amination was carried out for 35 h at 45 atm of hydrogen pressure in the presence of 1.5% by weight of a Ra—Ni catalyst with respect to the salan compound. The yield of the N,N'-bis(5-carboxy-2-hydroxybenzyl)ethylenediamine-N,N'-diacetic acid hydrochloride trihydrate was 37%.

The structure of the product was confirmed by means of ¹H NMR and the purity thereof by means of elemental microanalysis.

¹H NMR (DMSO) δ: 7.52-6.64 (m, 8H, ArH), 4.11 (s, 4H, HOOCCH$_2$N), 3.59 (s, 4H, ArCH$_2$N), 3.18 (s, 4H, NCH$_2$CH$_2$).

Elemental analysis: Calculated for C$_{22}$H$_{24}$N$_2$O$_{10}$.HCl3H$_2$O: C, 46.61; H, 5.51; N, 4.94,
Found: C, 46.65; H, 5.58; N, 4.89.

EXAMPLE 9

N,N'-bis(2-hydroxy-5-methylbenzyl)ethylenediamine-N,N'-diacetic acid monohydrochloride trihydrate The above product was prepared following the general procedure described in Example 5 and using 5-methylsalicylaldehyde as a starting material for the preparation of the salen compound. Condensation of with 5-methylsalicylaldehyde with ethylenediamine and reduction of the resulting salen compound to the salan compound were carried out in ethanol with the total yield 92%.

The salan product was isolated from the reaction mixture and reductive amination was carried out in water using 50% aqueous solution of glyoxylic acid and tributylamine at the molar ratio salan compound/glyoxylic acid/tributylamine equal to 1:3:3. The reductive amination was carried out for 48 h at 45 atm of hydrogen pressure in the presence of 1.5% by weight of a Ra—Ni catalyst with respect to the salan compound. The yield of the product N,N'-bis(2-hydroxy-5-methylbenzyl)ethylenediamine-N,N'-diacetic acid hydrochloride trihydrate was 75%.

The structure of the product was confirmed by means of ¹H NMR and the purity thereof by means of elemental microanalysis.

¹H NMR (DMSO) δ: 7.03-6.86 (m, 8H, ArH), 4.01 (s, 4H, HOOCCH$_2$N), 3.64 (s, 4H, ArCH$_2$N), 3.21 (s, 4H, NCH$_2$CH$_2$), 2.14 (s, 6H, CH$_3$Ar)

Elemental analysis: Calculated for C$_{22}$H$_{28}$N$_2$O$_6$.HCl.3H$_2$O:
C, 52.12; H, 6.96; N, 5.53. Found: C, 52.02; H, 7.01; N, 5.49.

EXAMPLE 10

N,N'-bis(2-hydroxy-5-methylbenzyl)ethylenediamine-N,N'-diacetic acid, sodium salt In a 50 ml beaker equipped with a mechanical stirrer 3 g (0.006 mol) of N,N'-bis(2-hydroxy-5-methylbenzyl)ethylenediamine-N,N'-diacetic acid monohydrochloride trihydrate prepared in Example 9 above and 24.5 ml of deionised water were introduced. Then 1 ml (0.018 mol) of the 50% NaOH aqueous solution was added dropwise. After stirring for 10 min a 10% aqueous solution of N,N'-bis(2-hydroxy-5-methylbenzyl)ethylenediamine-N,N'-diacetic acid sodium salt was obtained having the pH=11.5.

EXAMPLE 11

N,N'-bis(2-hydroxybenzyl)ethylenediamine-N,N'-diacetic acid, potassium salt

In a 50 ml beaker equipped with a mechanical stirrer 2.5 g (0.0057 mol) of N,N'-bis(2-hydroxybenzyl)ethylenediamine-N,N'-diacetic acid monohydrochloride trihydrate prepared in Example 6 above and 24.5 ml of deionised water were introduced. Then 1.72 ml (0.0171 mol) of the 40% NaOH aqueous solution was added dropwise. After stirring for 10 min a 8% aqueous solution of N,N'-bis(2-hydroxybenzyl)-ethylenediamine-N,N'-diacetic acid sodium salt, pH=12.2, was obtained.

The invention claimed is:

1. A process for the preparation of N,N'-bis(2-hydroxybenzyl)ethylenediamine-N,N'-diacetic acid and its derivatives of general formula I:

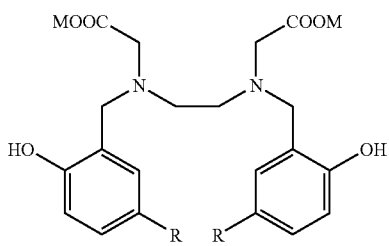

(I)

wherein:
both R have the same meaning and are selected from H, $C_1$-$C_4$alkyl, $CH_2OH$, $SO_3M$, and COOM; and
all M have the same meaning and represent hydrogen atom, Na, K or $NH_4$;
which comprises:
reductive amination of glyoxylic acid with a salan compound of general formula (II)

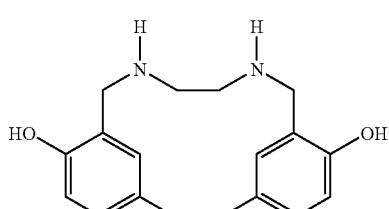

(II)

wherein R have the same meaning as defined for formula (I), by hydrogenation with hydrogen in the presence of a hydrogenation catalyst and an amine proton acceptor in a $C_1$-$C_3$ alkanol or their mixtures, a $C_1$-$C_3$ alkanol/water mixture or in water, to obtain the compound of formula (I), wherein M are hydrogen atoms, and if desired, converting it further into compound of formula (I), wherein M represent Na, K or $NH_4$ by the treatment with a corresponding base.

2. The process of claim 1 wherein said salan compound of formula (II) is prepared by reaction of ethylenediamine with 2 molar equivalents of a compound of formula (IV)

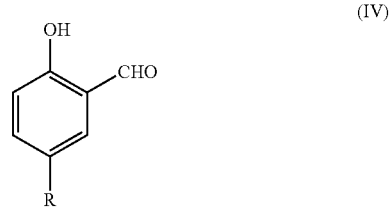

(IV)

wherein R are as described for formula (I) to obtain a corresponding salen compound of formula (V)

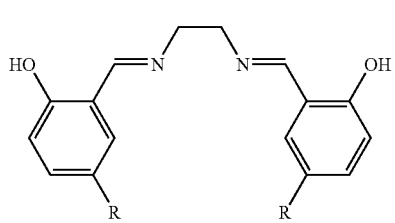

(V)

wherein R are as described for formula (I), and then reduction of the salen compound of formula (V) to obtain the compound of formula (II).

3. The process of claim 1 wherein a molar ratio compound of formula (II):glyoxylic acid:amine is in the range from 1:2:2 to 1:4:5.

4. The process of claim 1 wherein the amine proton acceptor is triethylamine.

5. The process of claim 1 wherein said hydrogenation catalyst is nickel, palladium or platinum on a solid support.

6. The process of claim 5 wherein said hydrogenation catalyst is Ra—Ni or Pd/C.

7. The process of claim 2 wherein R represent H.

8. The process of the claim 1 for the preparation of the compound of formula (I) wherein R is $C_1$-$C_4$alkyl wherein said salan compound of formula (II) is prepared by reaction of ethylenediamine, a formaldehyde source and a phenol compound of formula (III)

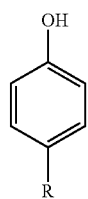

(III)

wherein R is $C_1$-$C_4$ alkyl in a molar ratio ethylenediamine:formaldehyde:phenol compound of about 1:2:2.

9. The process of claim 8 wherein R represent $CH_3$.

10. A process for the preparation of N,N'-bis(2-hydroxybenzyl)ethylenediamine-N,N'-diacetic acid and its derivatives of general formula I:

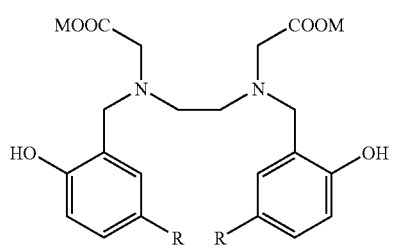

(I)

wherein:

both R have the same meaning and are selected from H, $C_1$-$C_4$alkyl, $CH_2OH$, $SO_3M$, and COOM; and all M have the same meaning and represent hydrogen atom, Na, K or $NH_4$;

which comprises:

a) reaction of ethylenediamine with 2 molar equivalents of a compound of formula (IV)

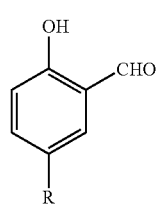

(IV)

wherein R is as defined for formula (I), to obtain a corresponding salen compound of formula (V)

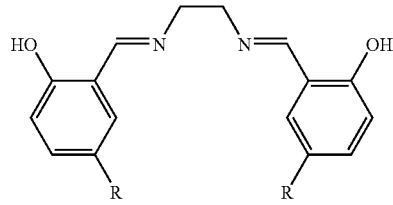

(V)

b) reduction of the salen compound of formula (V) to obtain a compound of formula (II)

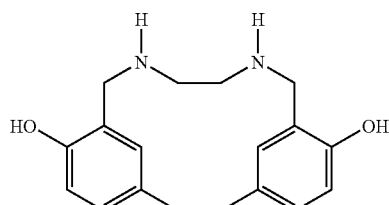

(II)

wherein R have the meanings as defined for formula (I), c) reductive amination of glyoxylic acid with the compound of formula (II) by hydrogenation with hydrogen in the presence of a hydrogenation catalyst and an amine proton acceptor in a $C_1$-$C_3$ alkanol or their mixtures, a $C_1$-$C_3$ alkanol/water mixture or in water, d) if desired, converting it further into compound of formula (I) wherein M represent Na, K or $NH_4$ by the treatment with a corresponding base.

11. The process of claim 10 wherein reduction in step b) is carried out by hydrogenation with hydrogen in the presence of a hydrogenation catalyst in a $C_1$-$C_3$ alkanol or their mixtures, a $C_1$-$C_3$ alkanol/water mixture, or in water.

12. The process of claim 10 wherein in step c) a molar ratio compound of formula (II):glyoxylic acid:amine is in the range from 1:2:2 to 1:4:5.

13. The process of claim 10 wherein in step c) said hydrogenation catalyst is nickel, palladium or platinum on a solid support.

14. The process of claim 13 wherein said hydrogenation catalyst is Ra—Ni or Pd/C.

15. The process of claim 11 wherein said reduction in step b) and reductive amination in step c) are carried out in the same reaction vessel, without isolation of the intermediate compound of formula (II).

16. The process of claim 11 wherein all steps a) to c) are carried out in the same reaction vessel, without isolation of intermediate compounds of formulas (V) and (II).

17. The process of claim 10 wherein R represent $CH_3$.

18. The process of claim 10 wherein R represent H.

19. A process for the preparation of N,N'-bis(2-hydroxybenzyl)ethylenediamine-N,N'-diacetic acid derivatives of general formula I:

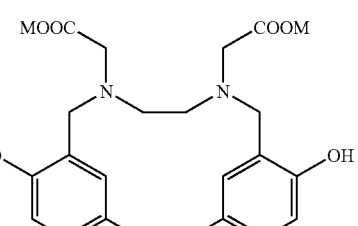

(I)

wherein both R have the same meaning and are selected from $C_1$-$C_4$alkyl; and all M have the same meaning and represent hydrogen atom, Na, K or $NH_4$;

which comprises:

a) reaction of ethylenediamine, a formaldehyde source and a phenol compound of formula (III)

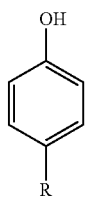

wherein R is $C_1$-$C_4$alkyl in a molar ratio ethylenediamine: formaldehyde: the phenol compound of about 1:2:2, to obtain a salan compound of general formula (II)

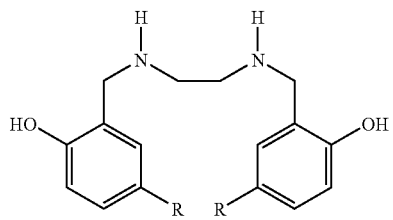

wherein R have the same meaning as defined above for formula (I), and b) reductive amination of glyoxylic acid with the compound of formula (II) by hydrogenation with hydrogen in the presence of a hydrogenation catalyst and an amine proton acceptor in a $C_1$-$C_3$ alkanol or their mixtures, a $C_1$-$C_3$ alkanol/water mixture or in water, c) if desired, converting it further into compound of formula (I), wherein M represent Na, K or $NH_4$ by the treatment with a corresponding base.

20. The process of claim 19 wherein in step a) said formaldehyde source is selected from an aqueous formaldehyde solution and paraformaldehyde.

21. The process of claim 20 wherein said formaldehyde source is the aqueous formaldehyde solution.

22. The process of claim 19 wherein in step b) a molar ratio compound of formula (II):glyoxylic acid:amine is in the range from 1:2:2 to 1:4:5.

23. The process of claim 20 wherein said molar ratio is about 1:3:3.5.

24. The process of claim 19 wherein in step b) said hydrogenation catalyst is nickel, palladium or platinum on a solid support.

25. The process of claim 24 wherein said hydrogenation catalyst is Ra—Ni or Pd/C.

26. The process of claim 19 wherein R represent $CH_3$.

* * * * *